United States Patent [19]

Joseph-Nathan et al.

[11] Patent Number: 4,803,284
[45] Date of Patent: Feb. 7, 1989

[54] PROCESSES FOR THE PREPARATION OF 3-AMINO-2-(5-METHOXY-1H-INDOL-3-YL) PROPIONIC ACID MONOHYDRATE

[75] Inventors: Pedro Joseph-Nathan; Martha S. Morales-Rios, both of Mexico City, Mexico

[73] Assignee: Centro de Investigacion y de Estudios Avanzados Del Instituto Politecnico Nacional, Mexico City, Mexico

[21] Appl. No.: 87,040

[22] Filed: Aug. 19, 1987

[51] Int. Cl.[4] .......................................... C07D 209/20
[52] U.S. Cl. .................................. 548/497; 548/494; 548/500; 548/501; 548/502; 548/495; 548/492
[58] Field of Search ...................... 548/492, 497, 494

[56] References Cited

U.S. PATENT DOCUMENTS

| | | | |
|---|---|---|---|
| 3,818,065 | 1/1974 | Schoellkopf et al. | 548/497 |
| 4,283,336 | 8/1981 | Schut et al. | 548/502 |
| 4,283,410 | 8/1981 | Schut et al. | 548/494 X |
| 4,393,081 | 7/1983 | Schut et al. | 548/495 X |

OTHER PUBLICATIONS

Safdy, et al., *J. Med. Chem.*, 25:723-739 (1982).
Juby, et al., *J. Med. Chem.*, 12396-401 (1969).
Walton, et al. *J. Med. Chem.*, 8:204-208 (1965).

Primary Examiner—David B. Springer
Attorney, Agent, or Firm—Holman & Stern

[57] ABSTRACT

The compound characterized by the structural Formula I:

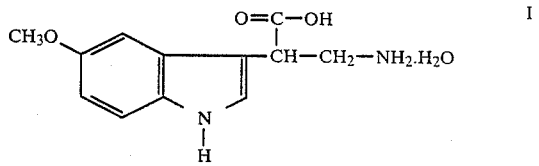

is therapeutically useful as an anti-hypertensive agent. A process for the preparation of the compound having Formula I and their synthetic intermediates is described. One of the synthetic intermediates is the compound characterized by the structural Formula:

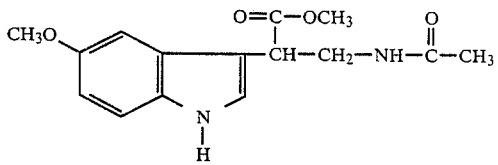

which is also therapeutically useful as an anti-hypertensive agent.

10 Claims, No Drawings

PROCESSES FOR THE PREPARATION OF 3-AMINO-2-(5-METHOXY-1H-INDOL-3-YL) PROPIONIC ACID MONOHYDRATE

BACKGROUND AND PRIOR ART

Schut et al. (U.S. Pat. No. 4,283,410[Aug. 11, 1981]; U.S. Pat. No. 4,283,336[Aug. 11, 1981]) and Safdy et al. (J. Medic. Chem. 25[6], 724 [1982]) have synthesized 3-amino-2-(5-methoxy-1H-indol-3-yl)propionic acid characterized by the structural formula:

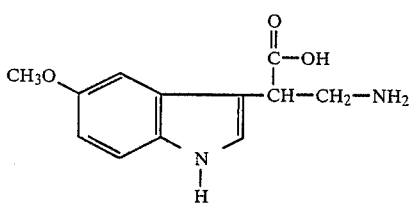

The authors state that the compound is therapeutically useful as an anti-hypertensive agent.

The synthesis of 3-amino-2-(5-methoxy-1H-indol-3-yl)propionic acid, reported in the two above cited patents and in the above cited publication, is a laborious and expensive sequence of reactions starting with 5-methoxyindole-3-acetonitrile characterized by the structural formula:

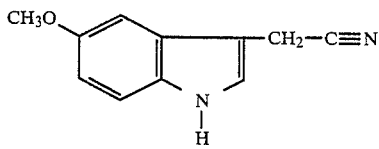

which is reated with an alkali metal base and acyloxylating agent to produce ethyl 2-cyano-2-(1-ethoxycarbonyl-5-methoxy-1H-indol-3-yl)acetate characterized by the structural formula:

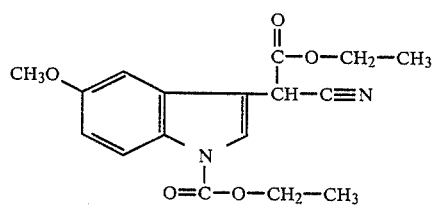

which is hydrogenated under pressure in the presence of a ctalyst in a solvent also acting as an acylating agent to provide ethyl 3-acetylamino-2-(1-ethoxycarbonyl-5-methoxy-1H-indol-3-yl)propanoate characterized by the structural formula:

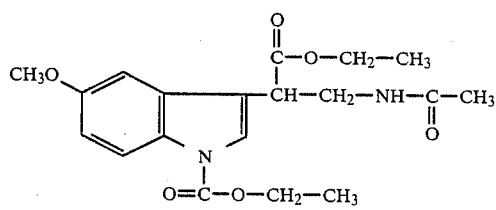

The above compound is hydrolyzed with an aqueous solution of an alkali metal hydroxide to produce a compound characterized by the formula:

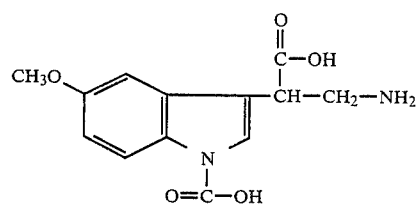

and then decarboxylated to produce the desired 3-amino-2-(5-methoxy-1H-indol-3-yl)propionic acid, whose structural formula is given above.

In turn, the authors prepared 5-methoxyindole-3-acetonitrile as JUBY and HUDYMA, J. Med. Chem. 12[2], 396[1969] from 5-methoxyindole under the reaction conditons reported by WALTON et al; J. Med. Chem. [2], 204[1965]. This requires the conversion of 5-methoxyindole into 3-formyl-5-methoxyindole, which is then transformed into 5-methoxygramine characterized by the formula:

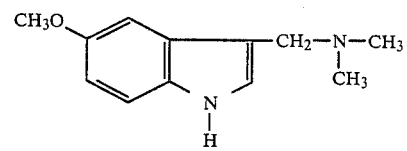

Treatment of 5-methoxygramine with methyl iodide gave the quaternary ammonium salt which after reaction with cyanide ion provided the desired 5-methoxyindole-3-acetonitrile whose structural formula is given above.

Looking further back for the synthesis of the required 5-methoxyindole, it becomes clear that para-methoxyphenylhydrazine can be reacted in an acid solution with pyruvic acid and the in situ formed para-methoxyphenylhydrazone converted into indole-2-carboxylic acid, which is then decarboxylated to afford 5-methoxyindole.

Later, Schut et al. (U.S. Pat. No. 4,393,081[Jul. 12, 1983]) also have synthesized methyl 3-acetylamino-2-(5-methoxy-1H-indol-3-yl)propanoate characterized by the structural formula:

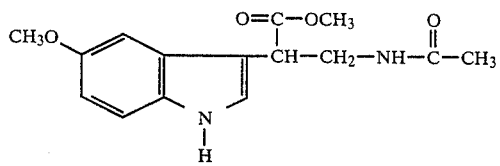

The authors state that the compound is also therapeutically useful as an anti-hypertensive agent.

The preparation of methyl 3-acetylamino-2-(5-methoxy-1H-indol-3-yl)propanoate, reported in U.S. Pat. No. 4,393,081, is done by either of two methods.

The first of these methods uses methyl 3-amino-2-(5-methoxy-1H-indol-3-yl)propanoate hydrochloride characterized by the structural formula:

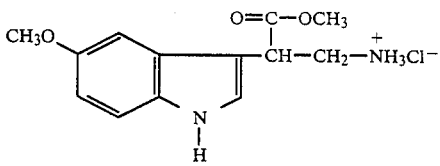

which is reacted with an acylating agent in the presence of an amine to provide methyl 3-acetylamino-2-(5-methoxy-1H-indol-3-yl)propanoate, whose structural formula is given above.

In turn, in U.S. Pat. No. 4,283,336 and in U.S. Pat. No. 4,283,410, the authors describe the preparation of methyl 3-amino-2-(5-methoxy-1H-indol-3-yl)propanoate hydrochloride, whose structural formula is given above, by treatment of 3-amino-2-(5-methoxy-1H-indol-3-yl)propionic acid, whose structural formula is given above, with an alcohol in the presence of an acid catalyst, followed by conversion of the reaction product into a salt by treatment with a mineral acid.

The second of these methods for the preparation of methyl 3-acetylamino-2-(5-methoxy-1H-indol-3-yl)propanoate uses 3-acetylamino-2-(5-methoxy-1H-indol-3-yl)propionic acid, characterized by the structural formula:

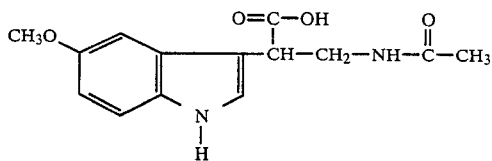

which is reacted with an alcohol in the presence of an acid catalyst to provide methyl 3-acetylamino-2-(5-methoxy-1H-indol-3-yl)propanoate, whose structural formula is given above.

In turn, in U.S. Pat. No. 4,283,336 and in U.S. Pat. No. 4,283,410, the authors describe the preparation of 3-acetylamino-2-(5-methoxy-1H-indol-3-yl)propionic acid, whose structural formula is given above, by treatment of ethyl 3-acetylamino-2-(1-ethoxycarbonyl-5-methoxy-1H-indol-3-yl)propanoate, whose structural formula is given above, with an aqueous solution of an alkali metal hydroxide, followed by neutralization of the solution with a mineral acid.

Thus, many reaction conditions have to be performed to convert para-methoxyphenyldrazine characterized by the structural formula:

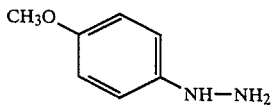

into the therapeutically useful compound 3-amino-2-(5-methoxy-1H-indol-3-yl)propionic acid having the structural formula given above, or into the therapeutically useful compound methyl 3-acetylamino-2-(5-methoxy-1H-indol-3-yl)propanoate having the structural formula given above.

SUMMARY OF THE INVENTION

The present invention involves a short synthetic process, which is more economic than that indicated in the background and prior art section above, for the obtention of the therapeutically useful compound 3-amino-2-(5-methoxy-1H-indol-3-yl)propionic acid monohydrate characterized by the structural Formula I.

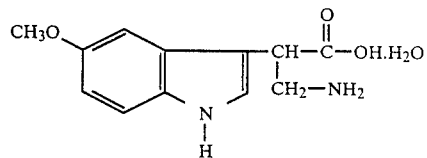

The process for preparing the compound having Formula I from the starting compound having Formula II

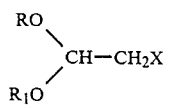

where R is a methyl group or an ethyl group, $R_1$ is a methyl group or an ethyl group, and X is chlorine, bromine or iodine comprises either the following steps:

(a) reacting a compound having Formula II with a compound having Formula III

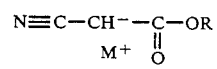

where R is a methyl group or an ethyl group, and $M^+$ is an alkali metal cation to produce a compound having Formula IV

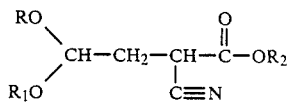

where R is a methyl group or an ethyl group, $R_1$ is a methyl group or an ethyl group, and $R_2$ is a methyl group or an ethyl group (b) hydrogenating the compound having Formula IV in the presence of a catalyst and an acylating agent to produce a compound having Formula V

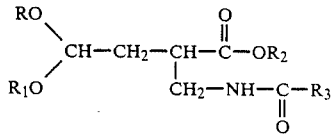

where R, $R_1$ and $R_2$ are as defined for Compound IV and $R_3$ is a methyl group, an ethyl group or a phenyl group (c) hydrolyzing the compound having Formula V with an aqueous acid solution to provide a compound having Formula VI

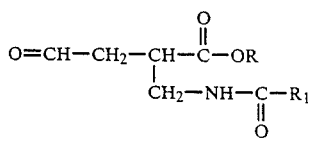

where R is a methyl group or an ethyl group and $R_1$ is a methyl group, an ethyl group or a phenyl group (d) reacting the compound having Formula VI with para-methoxyphenylhydrazine to provide a compound having Formula VII

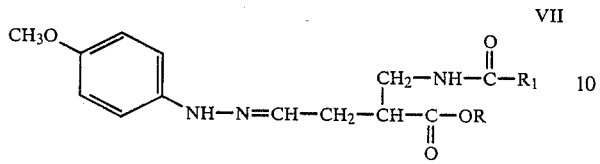
VII where R and $R_1$, are as defined for Compound VI (e) reacting the compound having Formula VII with an acid to provide a compound having Formula VIII

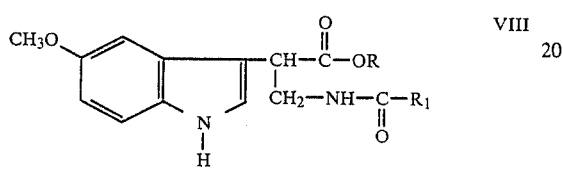
VIII where R and $R_1$ are as defined for Compound VII; and (f) hydrolyzing the compound having Formula VIII with an aqueous alkali metal hydroxide, acidifying the solution and isolating the desired product or alternatively, the process for preparing Compound I from Compound II comprises the following steps:

(g) step (a), above (h) hydrolyzing the compound having Formula IV, above, with an aqueous acid solution to provide Compound IX

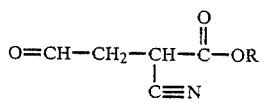
IX where R is a methyl group or an ethyl group (i) reacting the compound having Formula IX with para-methoxyphenylhydrazine to produce a compound having Formula X

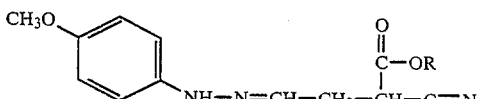
X where R is defined as for Compound IX (j) reacting the compound having Formula IX with an acid to provide a compound having Formula XI

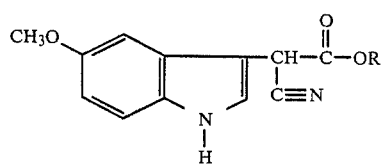
XI where R is defined as for Compound X (k) hydrogenating the compound having Formula XI in the presence of a catalyst and an acylating agent to produce a compound having Formula VIII, above; and (1) step (f), above, to isolate the desired product.

The process for preparing the compound having Formula I, also provides the therapeutically useful compound characterized by structural Formula VIII given above.

DETAILED DESCRIPTION OF THE INVENTION

The process for preparing the compound having Formula I

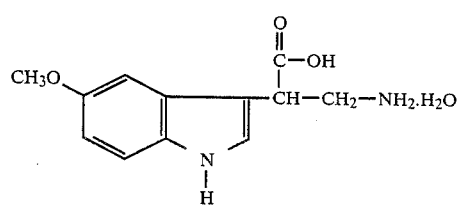
I begins by reacting a compound having Formula II

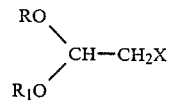
II where R is a methyl group or an ethyl group, $R_1$ is a methyl group or an ethyl group and X is chlorine, bromine or iodine with a compound having Formula III

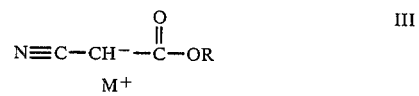
III where R is a methyl group or an ethyl group, and $M^+$ is an alkali metal cation to produce a compound having Formula IV

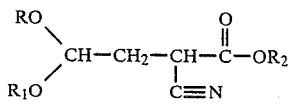
IV

In Formula IV, R is a methyl group or an ethyl group, $R_1$ is a methyl group or an ethyl group and $R_2$ is a methyl group or an ethyl group. The compound having Formula IV where R, $R_1$ and $R_2$ are methyl groups can be prepared as described in Example 1 below.

The alkali metal base used for the in situ preparation of Compound III may be sodium metal, lithium hydride, potassium methoxide, or the like. The reaction may be performed in a suitable solvent, such as benzene, N,N'-dimethylformamide, dimethoxyethane, or the like, or the solvent may be a mixture of the above mentioned comounds.

The molar ratios of the alkali metal base to the precursor of Compound III preferably range from about 11:10 to 10:11 respectively, with the latter ratio preferred. The preferred reagents are sodium hydride and methyl cyanoacetate. The reaction takes place in the temperature range of about 20° C. to 130° C. but it is preferred to have the temperature near 20° C. to avoid undesired side reactions like reductions.

Once the compound having Formula III is generated, it is immediately reacted with a compound having Formula II. In this process a carbon-halogen bond is broken and a carbon-carbon bond is formed, and therefore the reaction mass is heated near 100° C. to drive the reaction to completition. As a side product an inorganic salt, constituted by an alkali metal cation and an halogen anion, is formed. The preferred compound having Formula II is bromoacetaldehyde dimethyl acetal, the molar ratios of Compound II to Compound III range from about 10:9 to 9:10, with the latter ratio preferred and the preferred solvent for the reaction is the same as used for the generation of Compound III.

The compound having Formula IV is then isolated from the reaction mass, and is converted eighter to a compound having Formula IX below, or to a compound having Formula V

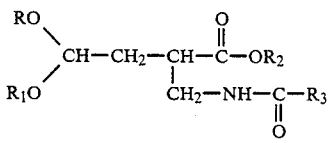

where R, $R_1$ and $R_2$ are as defined for Compound IV and $R_3$ is a methyl group, an ethyl group or a phenyl group.

For the conversion of compound having Formula IV to the compound having Formula V, the reduction of a cyano group into an aminomethyl group takes place by hydrogenation in the presence of a catalyst, and the newly formed aminomethyl group is protected with an acylating agent to avoid certain undesirable side reactions.

The compound having Formula V where R, $R_1$, $R_2$ and $R_3$ are methyl groups can be prepared as described in Example 2 below.

The conversion of the cyano group of Compound IV into the aminomethyl group of Compound V is performed with hydrogen under pressure in the presence of a catalyst such as Raney nickel, palladium or charcoal, rhodium on charcoal, platinum dioxide, or the like. The preferred catalyst is Raney nickel and the reduction is preferably performed in a suitable solvent such as acetyl chloride, propionyl chloride, benzoyl chloride, acetic anhydride, propionic anhydride, or the like, since these solvents also act as N-acylating agents which protect the aminomethyl group and thereby avoid undesired side reactions. The preferred solvent and acylating agent is acetic anhydride at a temperature from about 15° C. to about 70° C.

The compound having Formula V is then hydrolyzed with an aqueous acid solution such as hydrochloric acid, hydrobromic acid, sulfuric acid, trifluoroacetic acid, or the like, in a suitable solvent such as methanol, ethanol, tetrahydrofuran, dioxane, or the like at acid concentrations of about 0.1N to 10N, at a temperature of from about 20° C. to 100° C. during from about 1 to 60 minutes to provide a compound having Formula VI

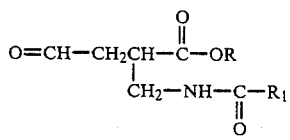

where R is a methyl group or an ethyl group and $R_1$ is a methyl group, an ethyl group or a phenyl group.

Our preferred method for the conversion of the dialkyl acetal group of Compound IV into the aldehyde group of Compound VI is by means of aqueous hydrochloric acid in tetrahydrofuran at above 60° C.

The compound having Formula VI is converted into the derived para-methoxyphenylhydrazone by treatment with para-methoxyphenylhydrazine or para-methoxyphenylhydrazine salts in a suitable solvent such as methanol, ethanol, tetrahydrofuran, dioxane, or the like in the presence of an aqueous acid solution such as hydrochloric acid, hydrobromic acid, sulfuric acid, trifluoroacetic acid, or the like at acid concentrations of about 0.1N to 10N at a temperature from about 20° C. to 100° C. during from about 5 to 100 minutes to provide a compound having Formula VII

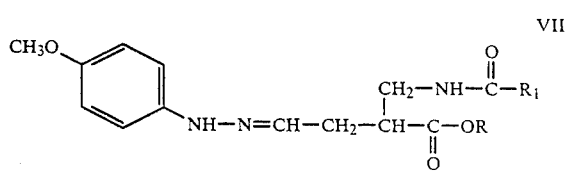

where R and $R_1$ are defined as for Compound VI.

Our preferred method for the conversion of the aldehyde group of Compound VI into the derived para-methoxyphenylhydrazone is by means of aqueous hydrochloric acid in tetrahydrofuran at about 70° C.

The compound having Formula VII is converted into the therapeutically useful indole derivative having Formula VIII

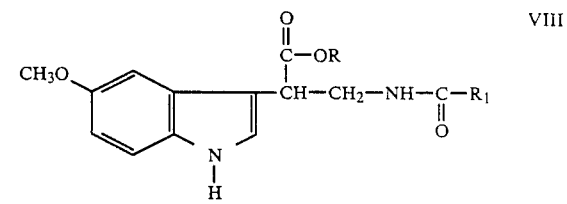

where R and $R_1$ are defined as for Compound VII. This transformation is achieved by treatment in a suitable solvent such as methanol, ethanol, tetrahydrofuran, dioxane, or the like with an aqueous acid solution such as hydrochloric acid, hydrobromic acid, sulfuric acid, trifluoroacetic acid, or the like at concentrations of about 0.1N to 10N at a temperature from about 20° C. to 100° C. during from about 20 to 120 minutes.

Our preferred method for the conversion of the para-methoxy phenylhydrazone of Compound VII into the indole derivative having Formula VIII is by means of aqueous hydrochloric acid in tetrahydrofuran at about 70° C.

It should be recognized by those skilled in the art that if the conversion of a compound having Formula V into a compound having Formula VI is performed under the same reaction conditions as the conversion of a compound having Formula VI into a compound having Formula VII, and that the conversion of a compound having Formula VII into a compound having Formula VIII is also performed under the same reaction conditions as the conversion of a compound having Formula V into a compound having Formula VI, then the separate reactions of hydrolyzing a dialkyl acetal group to provide an aldehyde group, of transforming an aldehyde group into the derived para-methoxyphenylhydrazone, and of converting a para-methoxyphenylhydrazone into an indole derivative can also be accomplished in one step. For example, our preferred mode combines the transformation of the compound having Formula V, where R, R$_1$, R$_2$ and R$_3$ are methyl groups, into the compound having Formula VIII, where R is a methyl group, as further described in Example 3 below.

Alternatively, the compound having Formula IV, above, is converted into a compound having Formula IX

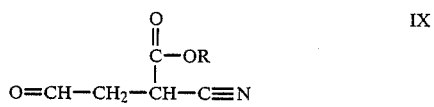

where R is a methyl group or an ethyl group.

The considerations and reaction conditions for the conversion of a compound having Formula IV into a compound having Formula IX are the same as those indicated above for the conversion of a compound having Formula V into a compound having Formula VI.

The compound having Formula IX is then converted into a compound having Formula X

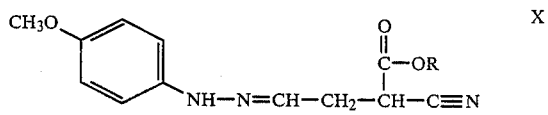

where R is defined as for Compound IX

The considerations and reaction conditions for the conversion of a compound having Formula IX into a compound having Formula X are the same as those indicated above for the conversion of a compound having Formula VI into a compound having Formula VII.

The compound having Formula X is then converted into a compound having Formula XI

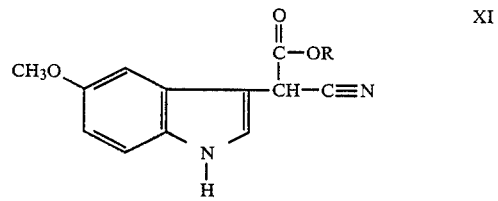

where R is defined as for Compound X.

The considerations and reaction conditions for the conversion of a compound having Formula X into a compound having Formula XI are the same as those indicated above for the conversion of a compound having Formula VII into a compound having Formula VIII.

It should be recognized by those skilled in the art that if the conversion of Compound V into Compound VIII through the intermediate compounds having Formulas VI and VII can be accomplished in a single step, then the conversion of a compound having Formula IV into a compound having Formula XI, through the intermediate compounds having Formula IX and X can also be accomplished in one step.

Our preferred method for the conversion of a compound having Formula IV, in which R, R$_1$, and R$_2$ are methyl groups, into a compound having Formula XI in which R is a methyl group is further illustrated in Example 4, below.

The compound having Formula XI is then hydrogenated to convert the cyano group into an aminomethyl group, which is immediately protected with an N-acylating agent to provide the therapeutically useful compound having Formula VIII, above.

The considerations for the conveniency to reduce the cyano of a Compound XI into an aminomethyl group and to protect the latter as an acylated derivative in a single step, are the same as those mentioned above for the conversion of a Compound IV into a Compound V. Our preferred mode of converting the compound having Formula XI, in which R is a methyl group, into the compound having Formula VIII, in which R and R$_1$ are methyl groups is further illustrated in Example 5, below.

The compound having Formula VIII is then hydrolized by means of an aqueous alkali metal hydroxide, such as sodium hydroxide, potassium hydroxide, or the like, at a concentration from about 3N to 11N, in about 1 to 15 hours at a temperature from about 50° C. to 105° C., and the resulting alkaline solution is then acidified to the isoelectric region of Compound I, at pH values from about 5.5 to 6.5 units, with an acid such as sulfuric acid, hydrochloric acid, hydrobromic acid acetic acid, trifluoroacetic acid, or the like. The compound having Formula I, is isolated preferably by filtration and purified by convenient means such as preferable crystallization. Our preferred mode is further illustrated in Example 6 below.

The preparation of the compounds of the prresent invention is further illustrated by the following examples

EXAMPLE 1

Preparation of methyl 2-cyano-4,4-dimethoxybutyrate (Compound IV)

A vigorously stirred suspension of sodium hydride (36 g, 1.5 mole) in a mixture of 1400 ml of anhydrous N,N-dimethylformamide and 450 ml of anhydrous benzene was cooled to −10° C. under an argon atmosphere and methyl cyanoacetate (163.5 g, 1.65 mole) dissolved in 150 ml of anhydrous benzene was added dropwise over a period of 60 minutes. The temperature of this solution was allowed to slowly reach the room temperature and further stirred for 60 minutes until all the sodium hydride dissolved. A solution of bromoacetaldehyde dimethyl acetal (228.2 g, 1.35 mole) was added at once and the temperature of the reaction mixture was slowly rised to about 100° C. over a period of 60 minutes and further maintained for additional 120 minutes until the precipitation of all NaBr occurred. The solution was filtered, and the filtrate was concentrated to a small volume by evaporation under vacuum and then partitioned between ether and water. The ether portion was washed with water, dried over anhydrous Na$_2$SO$_4$ which was then removed by filtration, and evaporated to leave a liquid residue. This liquid was distilled at reduced pressure. The fraction distilling at 65°–68° C. and 0.15 Torr was collected yielding 83.2 g (32.9% theory).

Anal. Calcd. for C$_8$H$_{13}$NO$_4$: C, 51.33; H, 7.00; N, 7.48; O 34.19, Found: C, 51.29; H, 6.85; N, 7.40; O, 34.31.

EXAMPLE 2

Preparation of methyl 4,4-dimethoxy-2-(N-methylacetamido) butyrate (Compound V)

A solution of Compound IV, prepared above, (10.0 g, 0.053 mole) in 250 ml of acetic anhydride was hydrogenated in the presence of about 10 g of Raney nickel as a catalyst under a pressure of about 50 psi during 20 hours. The catalyst was then removed by filtration, and the solvent was evaporated in vacuo to leave a thick syrup. This syrup was dissolved in 250 ml of ethyl acetate which was then washed with 5 ml of a saturated solution of potassium carbonate in water, then washed with water, and dried over anhydrous $Na_2SO_4$. After removing the $Na_2SO_4$ by filtration, the solvent was evaporated in vacuo and the thick syrup which remained was chromatographed on Silica get 62 with hexane-ethyl acetate (1:1 v:v) solvent and the solvent evaporated in vacuo to isolate the title compound in 80% yield, that is 9.98 g of a viscous colorless oil which decomposes when is attempted to distillate it at absolute pressures as low as 0.05 Torr.

Anal. Calcd. for $C_{10}H_{19}NO_5$: C, 51.49; H, 8.21; N, 6.00; O, 34.29, Found: C, 51.34; H, 8.02; N, 5.89; O, 34.55.

EXAMPLE 3

Preparation of methyl 3-acetylamino-2-(5-methoxy-1H-indol-3-yl)propionate (Comound VIII) from methyl 4,4-dimethoxy-2-(N-methylacetamido)butyrate (Compound V)

A vigorously stirred suspension of para-methoxyphenylhydrazine chlorhydrate (2.62 g, 0.015 mole) in 130 ml of tetrahydrofuran was heated to 60° C. under an argon atmoshere. Compound V, prepared above (5 g, 0.021 mole) was added at once and a solution of 6 ml of 10N hydrochloric acid in 35 ml of tetrahydrofuran was added over a period of 10 minutes. The reaction mixture was heated at reflux temperature for 45 minutes. The volume of the solution was reduced to one half by evaporation in vacuo and then extracted with ethyl acetate. The ethyl acetate portion was washed three times with saturated aqueous sodium bicarbonate, then three times with water and dried over anhydrous $Na_2SO_4$. After removing the $Na_2SO_4$ by filtration the solvent was evaporated in vacuo, and the thick brown syrup which remained was chromatographed on Silica gel 60 with hexane-ethyl acetate (1:1 v:v) solvent and the solvent evaporated in vacuo to isolate the compound in 40% yield, that is 1.74 g of a very viscous colorless oil which could not be crystallized and which decomposes when is attempted to distillate it at absolute pressures as low as 0.05 Torr.

Anal. Calcd. for $C_{15}H_{18}N_2O_4$: C, 62.06; H, 6.25; N, 9.65; O, 22.04, Found: C, 61.91; H, 6.34; N, 9.40; O, 22.19.

EXAMPLE 4

Preparation of methyl 2-cyano-2-(5-methoxy-1H-indol-3-yl)acetate (Compound XI)

A vigorously stirred suspension of para-methoxyphenylhydrazine chlorhidrate (6.47 g, 0.037 mole) in 260 ml of tetrahydrofuran was heated to 67° C. under an argon atmosphere. Compound IV, prepared above (10 g, 0.054 mole)was added at once and a solution of 12 ml of 10N hydrochloric acid in 70 ml of tetrahydrofuran was added over a period of 10 minutes. The reaction mixture was heated at reflux temperature for 35 minutes and further treated as described in Example 3. After chromatography on Silica gel 62 with hexane-ethyl acetate (3:1 v:v) solvent and evaporation of the solvent in vacuo, the viscous oily residue was crystallized from chloroform-hexane to yield 3.65 g (40.3%) of product mp 98°-100° C.

Anal. Calcd. for $C_{13}H_{12}N_2O_3$: C, 63.93; H, 4.95; N, 11.47; O, 19.65, Found: C, 63.81; H, 4.98; N, 11.40; O, 19.54.

EXAMPLE 5

Preparation of methyl 3-acetylamino-2-(5-methoxy-1H-indol-3-yl)propionate (Compound VIII) from methyl 2-cyano-2-(5-methoxy-1H-indol-3-yl)acetate (Compound XI)

A solution of Compound XI, prepared above (5 g, 0.020 mole) in 120 ml of acetic anhydride was hydrogenated as in Example 2, and the product isolated following the procedure therein. The compound was isolated in 92.5% yield, that is 5.5 g of a very viscous colorless oil which could not be crystallized and which decomposes when is attempted to distillate it at absolute pressures as low as 0.03 Torr. The compound is identical as the compound obtained in Example 3, above.

EXAMPLE 6

Preparation of 3-amino-2-(5-methoxy-1H-indol-3-yl)propionic acid monohydrate (Compound I)

A mixture of Compound VIII, prepared above, (4.06 g, 0.014 mole) and 14 ml of 10.75N NaOH was heated at reflux temperature, under an argon atmosphere and stirring for 8 hours. The mixture was diluted with 30 ml of water and acidulated with acetic acid to a pH value of 6.1. The solid was filtered and dissolved in 120 ml of hot water. Powdered charcoal was added and the mixture was heated to the boiling point and filtered to remove the charcoal. The clear filtrate was concentrated in vacuo until solid material was seen, and then cooled to 4° C. and stored over a period of 20 hours. The white solid that formed was removed by filtration, and dried over $CaCl_2$ to yield 2.03 g (57.5%), mp 206°-208° C. dec.

Anal. Calcd. for $C_{12}H_{14}N_2O_3.H_2O$: C, 57.13; H, 6.39; N, 11.10; O, 25.37. Found: C, 57.39; H, 6.42; N, 11.23; O, 25.18.

What is claimed is:

1. A process for preparing a therapeutically useful compound having Formula I

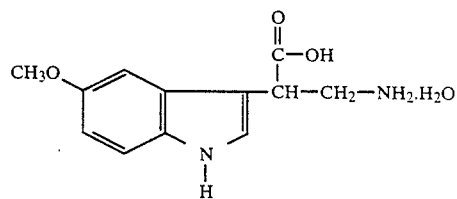

comprising the steps of:

(a) reacting a compound having Formula II

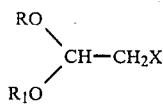   II where R is a methyl group or an ethyl group, R₁ is a methyl group or an ethyl group, and X is chlorine, bromine or iodine with a compound having Formula III

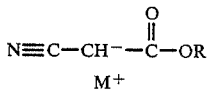   III where R is a methyl group or an ethyl group, and M⁺ is an alkali metal cation, in a suitable solvent at temperatures in the range of from about 40° C. to 130° C. to provide a compound having Formula IV

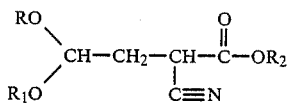   IV where R is a methyl group or an ethyl group, R₁ is a methyl group or an ethyl group, and R₂ is a methyl group or an ethyl group;
(b) separating Compound IV from the reaction mass;
(c) hydrogenating the compound having Formula IV under pressure, in the presence of a catalyst in a suitable solvent selected from the group of acetyl chloride, propionyl chloride, benzoyl chloride, acetic anhydride or propionic anhydride to produce a compound having Formula V

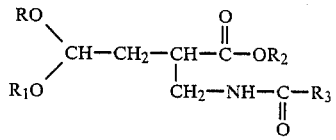   V where R, R₁ and R₂ are as defined for Compound IV, and R₃ is a methyl group, an ethyl group or phenyl group;
(d) separating Compound V from the reaction mass;
(e) hydrolyzing the compound having Formula V in a suitable solvent with an aqueous acid solution at concentrations of about 0.1N to 10N for about 1 to 60 minutes at temperatures of from about 20° C. to 100° C. to provide a compound having Formula VI

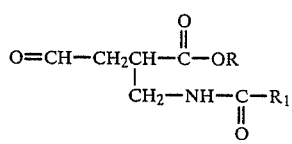   VI where R is a methyl group or an ethyl group and R₁ is a methyl group, an ethyl group or a phenyl group;
(f) reacting the compound having Formula VI with para-methoxyphenylhydrazine or para-methoxyphenyl hydrazine salts in a suitable solvent with an aqueous acid solution at concentrations of about 0.1N to 10N for about 5 to 100 minutes at temperatures of from about 20° C. to 100° C. to provide a compound having Formula VII

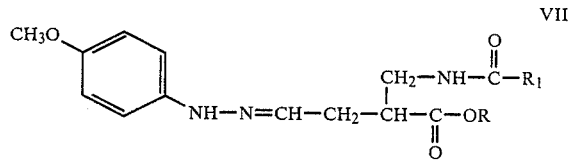   VII where R and R₁ are as defined for Compound VI;
(g) reacting the compound having Formula VII in a suitable solvent with an acid in aqueous solution at concentrations of about 1N to 10N for about 20 to 120 minutes at temperatures of from about 60° C. to 100° C. to provide a compound having Formula VIII

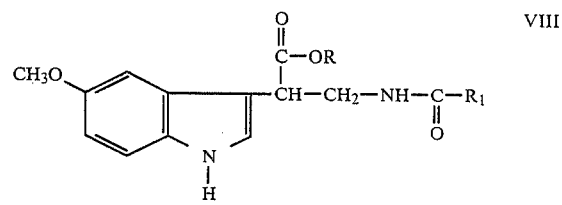   VIII where R and R₁ are as defined for Compound VII;
(h) separating Compound VIII from the reaction mass, and
(i) hydrolyzing the compound having Formula VIII with an aqueous alkali metal hydroxide at concentrations from about 3N to 11N for about 1 to 15 hours, at temperatures from about 60° C. to 105° C., acidifying the solution to the isoelectric region of Compound I at pH values from about 5.5 to 6.5 and isolating the compound having Formula I.

2. The process of claim 1 wherein the acylating agent is acetic anhydride.

3. The process of claim 1 wherein the catalyst is palladium or charcoal, rhodium on charcoal, Raney nickel or platinum dioxide.

4. The process of claim 1 wherein salts of para-methoxy phenylhydrazine are added to the reaction mixture or formed under the reaction conditions.

5. The process of claim 1 wherein the compound having Formula VIII is isolated.

6. A process for preparing a therapeutically useful compound having Formula I

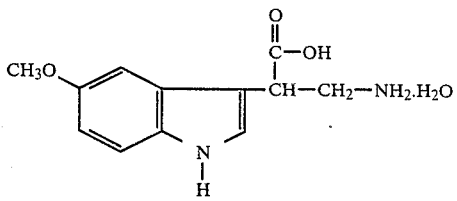   I comprising the steps of:
(a) reacting a compound having formula II

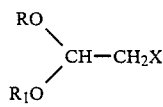

where R is a methyl group or an ethyl group, R₁ is a methyl group or an ethyl group, and X is chlorine, bromine or iodine with a compound having Formula III

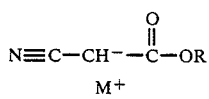

where R is a methyl group or an ethyl group, and M+ is an alkali metal cation, in a suitable solvent at temperatues in the range of from about 40° C. to 130° C. to provide a compound having Formula IV

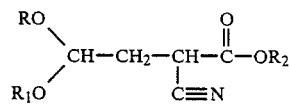

where R is a methyl group or an ethyl group, R₁ is a methyl group or an ethyl group, and R₂ is a methyl group or an ethyl group;
(b) Separating Compound IV from the reaction mass;
(c) hydrolyzing the compound having Formula IV in a suitable solvent with an aqueous acid solution at concentrations of about 0.1N to 10N for about 1 to 60 minutes at temperatures of from about 20° C. to 100° C. to provide a compound having Formula IX

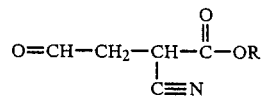

where R is a methyl group or an ethyl group;
(d) reacting the compound having Formula IX with para-methoxyphenylhyrazine or para-methoxyphenylhydrazine salts in a suitable solvent with an aqueous acid solution at concentrations of about 0.1N to 10N for about 5 to 100 minutes at temperatures of from about 20° C. to 100° C. to provide a compound having Formula X

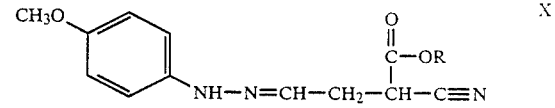

where R is as defined for Compound IX;
(e) reacting the compound having Formula X in a suitable solvent with an aqueous acid solution at concentrations of about 1N to 10N for about 20 to 120 minutes at temperatures of from about 60° C. to 100° C. to provide a compound having Formula XI

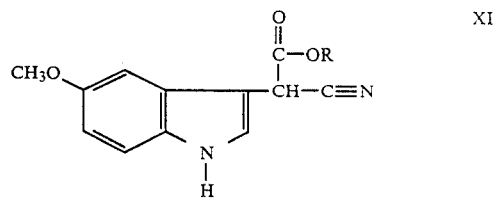

where R is defined as for Compound X;
(f) separating Compound XI from the reaction mass;
(g) hydrogenating the compound having Formula XI under pressure, in the presence of a catalyst, in a suitable solvent selected from the group of acetyl chloride, propionyl chloride, benzoyl chloride, acetic anhydride or propionic anhydride to produce a compound having Formula VIII;

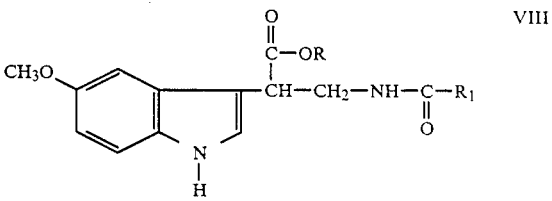

R is a methyl group or an ethyl group and R₁ is a methyl group, an ethyl group or a phenyl group;
(h) separating Compound VIII from the reaction mass, and
(i) hydrolyzing the compound having Formula VIII with an aqueous alkali metal hydroxide at concentrations from about 3N to 11N for about 1 to 15 hours, at temperatures from about 60° C. to 105° C., acidifying the solution to the isoelectric region of Compound I at pH values from about 5.5 to 6.5 and isolating the compound having Formula I.

7. The process of claim 6 wherein the acylating agent is acetic anhydride.

8. The process of claim 6 wherein the catalyst is palladium on charcoal, rhodium on charcoal, Raney nickel or platinum dioxide.

9. The process of claim 6 wherein salts of para-methoxy phenylhydrazine are added to the reaction mixture or formed under the reaction conditions.

10. The process of claim 6 wherein the compound having Formula VIII is isolated.

* * * * *